(12) United States Patent
Morris et al.

(10) Patent No.: US 8,835,478 B2
(45) Date of Patent: Sep. 16, 2014

(54) TREATMENT FOR CANCER

(75) Inventors: David L. Morris, Lugarno (AU); Mohammad Hossein Pourgholami, Penshurst (AU)

(73) Assignee: Pitney Pharmaceuticals PTY Limited, Sydney (AU)

( * ) Notice: Subject to any disclaimer, the term of this patent is extended or adjusted under 35 U.S.C. 154(b) by 0 days.

(21) Appl. No.: 13/457,860

(22) Filed: Apr. 27, 2012

(65) Prior Publication Data

US 2012/0214856 A1    Aug. 23, 2012

Related U.S. Application Data

(62) Division of application No. 11/720,884, filed as application No. PCT/AU2005/001839 on Dec. 6, 2005, now abandoned.

(51) Int. Cl.
 *A61K 31/337* (2006.01)
 *A61K 31/4184* (2006.01)
 *A61K 31/427* (2006.01)

(52) U.S. Cl.
 CPC ............ *A61K 31/427* (2013.01); *A61K 31/337* (2013.01); *A61K 31/4184* (2013.01)
 USPC ......................................... 514/395; 514/449

(58) Field of Classification Search
 CPC .................... A61K 31/4184; A61K 31/337
 See application file for complete search history.

(56) References Cited

U.S. PATENT DOCUMENTS 5,900,429 A * 5/1999 Camden .................... 514/395
2004/0058972 A1 * 3/2004 Davis ....................... 514/394

FOREIGN PATENT DOCUMENTS

| WO | WO 98/51303 A1 | 11/1998 |
| WO | WO 00/41669 A2 | 7/2000 |
| WO | WO 01/12169 A2 | 2/2001 |
| WO | WO 02/058697 A1 | 8/2002 |
| WO | WO 02/076454 A1 | 10/2002 |

OTHER PUBLICATIONS

Sasaki, J. et al. 2002 "The anthelmintic drug medendazole induces mitotic arrest and apoptosis by depolymerizing tubulin in non-small cell lung cancer cells" *Molec Cancer Therapeutics* 1:1201-1209.
Tahir, S.K. et al. 2001 "A-204197, a new tubulin-binding agent with antimitotic activity in tumor cell lines resistant to known microtubule inhibitors" *Cancer Research* 61: 5480-5485.

* cited by examiner

*Primary Examiner* — James D Anderson
(74) *Attorney, Agent, or Firm* — Knobbe, Martens Olson & Bear, LLP

(57) ABSTRACT

The present invention provides methods for the treatment of tumors, comprising administration of an effective amount of at least one taxoid and an effective amount of at least one benzimidazol carbamate compound of formula (I). The invention also provides a method for the treatment of tumors insensitive to one or more anti-mitotic drugs, the method comprising administering a effective amount of at least one benzimidazole carbamate compound of formula (I). Also provide are compositions for carrying out methods of the invention.

10 Claims, 5 Drawing Sheets

A

B

A

B

A

B

C

A

B

TREATMENT FOR CANCER

TECHNICAL FIELD

The present invention relates generally to methods and compositions for the treatment of tumours.

BACKGROUND OF THE INVENTION

Paclitaxel and docetaxel are members of the taxoid family of anti-mitotic drugs widely used as chemotherapeutic agents. Taxoids promote microtubule polymerization and stabilization. Their anti-mitotic properties are derived from their ability to bind tubulin and disrupt microtubule dynamics thereby inducing mitotic arrest and cell death.

Paclitaxel has activity against a broad band of tumour types, including breast, ovarian, lung, head and neck cancers. Paclitaxel also has activity in other malignancies that are refractory to conventional chemotherapy, including previously-treated lymphoma and small cell lung cancers and oesophageal, gastric, endometrial, bladder and germ cell tumours (Mekhail and Markman, 2002; Yamazaki et al., 1998). It is one of the most unique, and successful, chemotherapeutic agents currently used in the clinic for cancer treatment. However major problems associated with paclitaxel therapy exist. One of these is toxicity. Common toxicities of paclitaxel include total alopecia, hypersensitivity reactions, bone marrow suppression (principally neutropenia), arthralgia, myalgias, and peripheral neuropathy (Markman, 2003). The development of tolerance or drug resistance in tumour cells to paclitaxel is also a significant factor hindering the ongoing efficacy of paclitaxel treatment. To overcome resistance, typically the dosages of paclitaxel administered are increased thus leading to the development of side effects.

Accordingly, there is a clear need for alternative improved strategies for taxoid-based cancer treatments.

Another group of agents that target microtubules are the benzimidazole carbamates that have an opposing mode of action to the taxoids in that they inhibit microtubule polymerization rather than polymerize tubulin (Lacey, 1990; Lacey and Gill, 1994). Benzimidazole carbamates include albendazole, a broad spectrum anthelmintic used clinically for the treatment of a number of parasitic infections (Horton, 2000). The present inventors have previously found that albendazole has an anti-proliferative effect on a range of cancer cell lines in vitro and on cancers in animal models and clinical studies (WO 02/076454, the disclosure of which is incorporated herein by reference).

As disclosed herein, the present inventors have now surprisingly found that cancer cells highly resistant to paclitaxel and partially resistant to vincristine and colchicine are in fact hypersensitive to the anti-proliferative effects of albendazole. Further, albendazole potentiates the effect of paclitaxel in human cancer cells, both in paclitaxel-sensitive and paclitaxel-resistant cell lines, such that used in combination these drugs have an additive or synergistic effect in inhibiting cancer cell proliferation.

SUMMARY OF THE INVENTION

According to a first aspect of the present invention there is provided a method for the treatment of a tumour in a subject, the method comprising administering to the subject an effective amount of at least one taxoid and an effective amount of at least one benzimidazole carbamate compound of formula I:

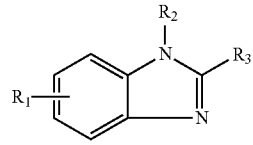

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, —$SR_{14}$, —$OR_{15}$, —$SOR_{16}$, —$SO_2R_{17}$, —SCN, —C(O)—$R_{18}$, $NR_{20}COOR_{21}$, where $R_{15}$ to $R_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl;

or a metabolite, derivative or analogue thereof.

The $R_1$ substitution may occur in the 5 or 6 position.

The benzimidazole carbamate compound may be a compound of Formula II:

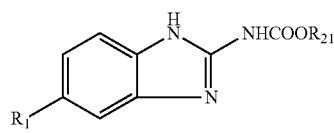

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_{21}$ is H, substituted or unsubstituted, straight or branch chain alkyl, alkenyl, alkenylalkyl, cycloalkyl, cycloalkylalkyl, cycloakenylalkyl, aryl or arylalkyl.

The benzimidazole carbamate compound may be a compound of Formula III:

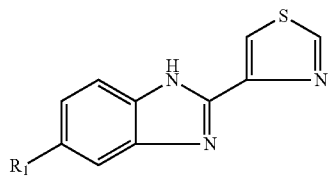

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4.

The benzimidazole carbamate compound may be selected from the group consisting of albendazole, albendazole sulphoxide, mebendazole, flubendazole, triclabendazole, oxfenbendazole, luxabendazole, cambendazole, oxibendazole, parbendazole, thiabendazole, cyclobendazole, dribendazole, etibendazole and fenbendazole.

In one embodiment the benzimidazole carbamate compound is albendazole, or a metabolite, derivative or analogue thereof.

The taxoid may be paclitaxel, docataxel, or a metabolite, derivative or analogue thereof.

The tumour may be a liver, ovarian, colorectal, lung, small cell lung, breast, prostate, pancreatic, renal, gastric, endometrial, oesophageal, head or neck tumour, peritoneal carcinomatosis, leukaemia, lymphoma, sarcoma or secondary metastases thereof.

The tumour may be insensitive to treatment with one or more antimitotic drugs. The one or more antimitotic drugs may be selected from a taxoid, a Vinca alkaloid and a colchicinoid. In one embodiment the tumour is a taxoid-insensitive tumour. According to this embodiment, the amount of taxoid administered may be an amount otherwise ineffective to treat the tumour if administered alone.

The taxoid and the benzimidazole carbamate compound may be administered simultaneously or sequentially. Accordingly, the taxoid and the benzimidazole carbamate compound may be present in a single pharmaceutical composition or in separate compositions. The taxoid and the benzimidazole carbamate compound may be administered systemically.

According to a second aspect of the present invention there is provided a method for the treatment of a tumour in a subject, the method comprising administering to the subject an effective amount of paclitaxel and an effective amount of albendazole.

The paclitaxel and albendazole may be administered simultaneously or sequentially. Accordingly, the paclitaxel and albendazole may be present in a single pharmaceutical composition or in separate compositions. The taxoid and the benzimidazole carbamate compound may be administered systemically.

According to a third aspect of the present invention there is provided a method for the treatment of a taxoid-insensitive tumour in a subject, the method comprising systemically administering to the subject paclitaxel and an effective amount of albendazole. The amount of paclitaxel administered may be an amount otherwise ineffective to treat the tumour if administered alone.

According to a fourth aspect of the present invention there is provided a pharmaceutical composition comprising at least one taxoid and at least one benzimidazole carbamate compound of formula I:

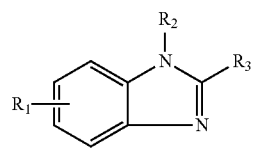

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, —$SR_{14}$, —$OR_{15}$, —$SOR_{16}$, —$SO_2R_{17}$, —SCN, —C(O)—$R_{18}$, —$OR_{19}$, $NR_{20}COOR_{21}$, where $R_{15}$ to $R_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl;

or a metabolite, derivative or analogue thereof.

The $R_1$ substitution may occur in the 5 or 6 position.

The benzimidazole carbamate compound may be a compound of Formula II:

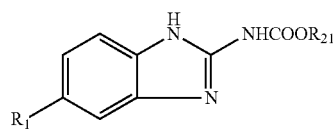

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_{21}$ is H, substituted or unsubstituted, straight or branch chain alkyl, alkenyl, alkenylalkyl, cycloalkyl, cycloalkylalkyl, cycloakenylalkyl, aryl or arylalkyl.

The benzimidazole carbamate compound may be a compound of Formula III:

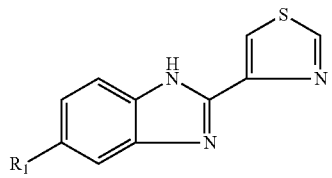

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, B'$(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4.

The benzimidazole carbamate compound may be selected from the group consisting of albendazole, albendazole sulphoxide, mebendazole, flubendazole, triclabendazole, oxfendazole, luxabendazole, cambendazole, oxibendazole, parbendazole, thiabendazole, cyclobendazole, dribendazole, etibendazole and fenbendazole.

In one embodiment the benzimidazole carbamate compound is albendazole, or a metabolite, derivative or analogue thereof.

The taxoid may be paclitaxel, docataxel, or a metabolite, derivative or analogue thereof.

The composition may further comprise one or more pharmaceutically acceptable carriers, adjuvants or diluents.

According to a fifth aspect of the present invention there is provided a pharmaceutical composition comprising paclitaxel and albendazole.

The composition may include one or more pharmaceutically acceptable carriers, adjuvants or diluents.

According to a sixth aspect of the present invention there is provided a composition for the is treatment of a tumour in a subject, the composition comprising at least one taxoid and at least one benzimidazole carbamate compound of formula I.

The tumour may be a liver, ovarian, colorectal, lung, small cell lung, breast, prostate, pancreatic, renal, gastric, endometrial, oesophageal, head or neck tumour, peritoneal carcinomatosis, leukaemia, lymphoma, sarcoma or secondary metastases thereof.

The tumour may be insensitive to treatment with one or more antimitotic drugs. The one or more antimitotic drugs may be selected from a taxoid, a Vinca alkaloid and a colchicinoid. In one embodiment the tumour is a taxoid-insensitive tumour.

According to a seventh aspect of the present invention there is provided a composition for the treatment of a taxoid-insensitive tumour in a subject, the composition comprising paclitaxel and albendazole.

According to an eighth aspect of the present invention there is provided a method for the treatment of a tumour in a subject, the method comprising administering to the subject an effective amount of a composition according to the third, fourth or fifth aspect.

According to a ninth aspect of the present invention there is provided a use of at least one taxoid and at least one benzimidazole carbamate compound of formula I for the manufacture of a medicament for the treatment of a tumour in a subject.

According to a tenth aspect of the present invention there is provided a method for the treatment of a tumour in a subject, wherein the tumour is insensitive to one or more anti-mitotic drugs, the method comprising administering to the subject an effective amount of at least one benzimidazole carbamate compound of formula I:

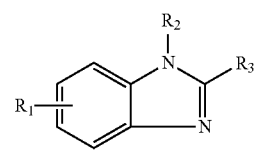

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, B'$(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, —$SR_{14}$, —$OR_{15}$, —$SOR_{16}$, —$SO_2R_{17}$, —SCN, —C(O)—$R_{18}$, —$OR_{19}$, $NR_{20}COOR_{21}$, where $R_{15}$ to $R_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl;

or a metabolite, derivative or analogue thereof.

The tumour may be insensitive to one or more of a taxoid, a Vinca alkaloid and a colchicinoid. The taxoid may be paclitaxel. The Vinca alkaloid may be vincristine. The colchicinoid may be colchicine. In one embodiment the tumour is insensitive to at least paclitaxel.

According to an eleventh aspect of the present invention there is provided the use of at least one benzimidazole carbamate compound of formula I for the manufacture of a medicament for the treatment of a tumour insensitive to at least one anti-mitotic drug.

In the aspects and embodiments of the invention described above the subject is typically human.

Also contemplated within the above aspects and embodiments are isomers, including stereoisomers and geometric isomers of the compounds of Formula I, II and III, as well as tautomeric forms thereof.

DEFINITIONS

In the context of this specification, the term "comprising" means "including principally, but not necessarily solely". Furthermore, variations of the word "comprising", such as "comprise" and "comprises", have correspondingly varied meanings.

As used herein the terms "treating" and "treatment" refer to any and all uses which remedy a condition or symptoms, prevent the establishment of a condition or disease, or otherwise prevent, hinder, retard, or reverse the progression of a condition or disease or other undesirable symptoms in any way whatsoever.

As used herein the term "effective amount" includes within its meaning a non-toxic but sufficient amount of an agent or compound to provide the desired effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the term "insensitive" refers to a tumour or portion thereof which is refractory, to some degree, to treatment with a particular therapeutic agent. The term "'insensitive" therefore is used to describe tumours otherwise referred to as resistant, for example paclitaxel-resistant. However this term is not limited to tumours which show complete or even significant levels of resistance to the therapeutic agent in question, but rather includes within its scope tumours that retain sensitivity to the agent but which display a diminished responsiveness to the agent when compared to sensitive tumours.

The term "alkyl" as used herein, includes within its meaning monovalent, saturated, straight and branched chain hydrocarbon radicals.

The term "alkenyl" as used herein, includes within its meaning, monovalent, straight and branched chain hydrocarbon radicals having at least one double bond.

The term "aryl" as used herein, includes within its meaning monovalent, single, polynuclear, conjugated and fused aromatic hydrocarbon radicals.

BRIEF DESCRIPTION OF THE DRAWINGS

The present invention will now be described, by way of example only, with reference to the following drawings.

BEST MODE OF PERFORMING THE INVENTION

Figure 1:
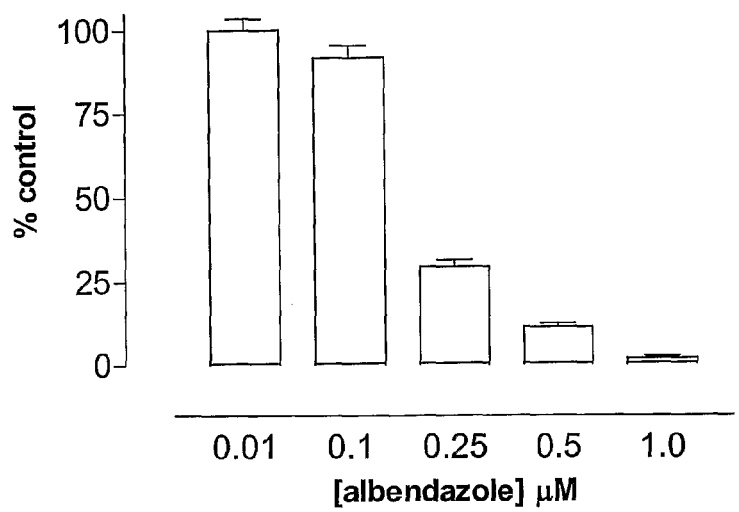
FIG. 1: Cytotoxic activity of albendazole and paclitaxel in inhibiting proliferation of OVCAR-3 cells in vitro. (A) Dose-response inhibition of cell proliferation by albendazole alone. (B) Dose-related inhibition of proliferation by paclitaxel and potentiation of this effect when cells were co-incubated with 0.25 µM albendazole. Cell proliferation was measured using a sulforhodamine B assay. Results are presented as the % of control (vehicle treated cells).
Figure 1:
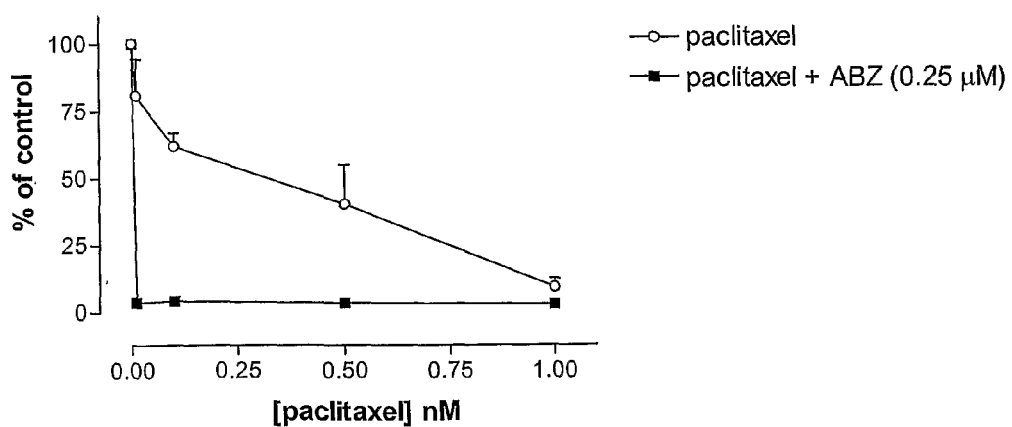

Dose-related toxicity and resistance are significant factors limiting the adoption and efficacy of treatment of patients with cancer using antmitotic drugs such as paclitaxel. The strategy of increasing the dose of paclitaxel to overcome resistance merely exacerbates the problems of paclitaxel toxicity and the occurrence of side effects, while also potentially promoting the development of increased drug resistance. There is a clear need for strategies to maximise the benefits of paclitaxel, and other taxoid, treatments of tumours to increase drug efficacy without the need to increase dosages.

As disclosed herein, the present inventors have now found that albendazole potentiates the effect of paclitaxel in inhibiting proliferation of human cancer cells. The effect is observed both in paclitaxel-sensitive and paclitaxel-resistant human cancer cells. The inventors have also demonstrated that the paclitaxel-resistant tumour cells are hypersensitive to albendazole, a member of a different class of anti-tubulin agents. This is a particularly surprising finding as one skilled in the art would expect that a cell resistant to one type of anti-tubulin agent would be equally resistant to another. The inventors have demonstrated that this is not necessarily the case.

Accordingly, in the clinical setting the addition of albendazole to paclitaxel may lead to a reduction of the paclitaxel dose required to produce an antitumour effect. Furthermore, in paclitaxel resistant tumours, the use of albendazole, either in the presence or absence of a paclitaxel treatment regimen may lead to tumour responsiveness and thus a beneficial therapeutic effect previously unattainable. As exemplified herein, typically in paclitaxel-resistant cell lines an approximately 50-fold increase in paclitaxel concentration is required to achieve a similar response to that observed in paclitaxel-sensitive cells. However the inventors demonstrate here that in the presence of albendazole this paclitaxel concentration can be reduced by about 25 to 50-fold to achieve a similar response to that observed in paclitaxel-sensitive cells. That is, the addition of to albendazole to an otherwise ineffective dose of paclitaxel can produce a beneficial response.

Accordingly, one aspect of the present invention provides a method for the treatment of a tumour in a subject, the method comprising administering to the subject an effective amount of at least one taxoid and an effective amount of at least one benzimidazole carbamate compound of formula I:

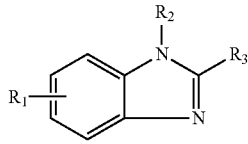

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, —$SR_{14}$, —$OR_{15}$, —$SOR_{16}$, —SCN, —$SO_2R_{17}$, —C(O)—$R_{18}$, —$OR_{19}$, $NR_{20}COOR_{21}$, where $R_{15}$ to $R_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl; or an analogue, metabolite or derivative thereof.

Typically the benzimidazole carbamate compound is a compound of formula II

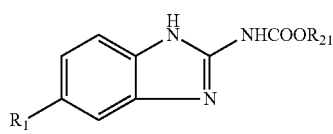

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_{21}$ is H, substituted or unsubstituted, straight or branch chain alkyl, alkenyl, alkenylalkyl, cycloalkyl, cycloalkylalkyl, cycloakenylalkyl, aryl or arylalkyl, or of formula III

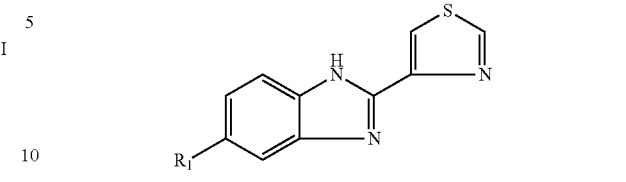

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4.

Those skilled in the art will readily appreciate that isomers, including stereoisomers and geometric isomers, of the above described benzimidazole carbamate compounds may exists and the use of such isomers are included within the scope of the present invention. Further, the use of tautomeric forms of the above compounds is also contemplated. For example the substituted benzimidazole group may exist in a number of tautomeric forms, including where the $R_u$ substituent is in any one of the 4 to 7 positions.

As disclosed herein, the inventors have also found that cancer cells highly resistant to paclitaxel and partially resistant to vincristine and colchicine are hypersensitive to the anti-proliferative effects of albendazole. This opens previously unrealised avenues for the treatment of tumours resistant or insensitive to anti-mitotic drugs by using benzimidazole carbamates such as albendazole. At present resistance is combated by increasing the dosage of the agent to which resistance has developed, thereby increasing the risk of side effects such as toxicity and leading to the development of greater resistance and failure of the therapy. The clinical application of benzimidazole carbamates in the treatment of tumours resistant to drugs such as paclitaxel overcomes these inherent deficiencies in the prior art approach.

Accordingly, an aspect of the present invention provides a method for the treatment of a tumour in a subject, wherein the tumour is insensitive to one or more anti-mitotic drugs, the method comprising administering to the subject an effective amount of at least one benzimidazole carbamate compound of formula I, II or III as defined above. For example, the tumour may show complete or partial resistance to one or more of the following: taxanes, Vinca alkaloids and colchicinoids, or derivatives or analogues thereof.

Albendazole or a metabolite, derivative or analogue thereof (such as albendazole sulphoxide or albendazole sulfone) is one benzimidazole carbamate particularly useful in the methods and is compositions of the present invention. However it will be readily appreciated by those skilled in the art that other benzimidazole carbamates may also be employed. For example other suitable benzimidazole carbamates include, but are not limited to, mebendazole, flubendazole, triclabendazole, oxfenbendazole, luxabendazole, cambendazole, oxibendazole, parbendazole, thiabendazole, cyclobendazole, dribendazole, etibendazole and fenbendazole.

Typically in methods and compositions of the invention employing the use of taxoids, the taxoid is paclitaxel or a metabolite, derivative or analogue thereof, or doclitaxel or a metabolite, derivative or analogue thereof. However it will be readily appreciated by those skilled in the art that other taxoids may also be employed. For example a large number of derivatives of paclitaxel and docataxel are currently in the experimental phase or in clinical trial. It will be understood by those skilled in the art that such derivatives are within the scope of the methods and compositions of the invention.

The present invention further provides pharmaceutical compositions comprising at least one taxoid and at least one benzimidazole carbamate compound of formula I. Typically these compositions are used according to the methods of the invention.

It will be readily appreciated by those skilled in the art that according to the methods of the present invention each component of the combination may be administered at the same time, or sequentially in any order, or at different times, so as to provide the desired therapeutic effect. When administered separately, it may be preferred for the components to be administered by the same route of administration, although it is not necessary for this to be so. Alternatively, the components may be formulated together in a single dosage unit as a combination product.

The methods of the present invention may further comprise the administration of one or more corticosteroids and/or antihistamines (such as diphenydramine), for example as a pretreatment, to counteract the risk of the patient having an adverse reaction to the taxoid. Similarly, the methods of the invention may comprise the administration of one or more potentiators of the effect of the taxoid and/or benzimidazole carbamate compound on the tumour to be treated. Such administration may be concomitant with the administration of either or both of the taxoid and the benzimidazole carbamate compound. For example, a suitable potentiator of benzimidazole carbamates is an isoquinoline such as praziquantel.

Tumours

Those skilled in the art will readily appreciate that the methods and compositions of the present invention find application in the treatment of any tumour type amenable to treatment with taxoids and benzimidazole carbamates independently. For example the tumours which may be treated using methods and compositions of the present invention include liver, ovarian, colorectal, lung, small cell lung, breast, prostate, pancreatic, renal, gastric, endometrial, oesophageal, head or neck tumours, peritoneal carcinomatosis, leukaemia, lymphomas, sarcomas or secondary metastases thereof.

Further those skilled in the art will appreciate that the present invention finds particular application in the treatment of taxoid resistant tumours, such as paclitaxel resistant tumours, as well as tumours resistant to treatment with Vinca alkaloids or colchicinoids.

Compositions and Routes of Administration

According to the methods of present invention compounds and compositions may be administered by any suitable route, either systemically, regionally or locally. The particular route of administration to be used in any given circumstance will depend on a number of factors, including the nature of the tumour to be treated, the severity and extent of the tumour, the required dosage of the particular compounds to be delivered and the potential side-effects of the compounds.

For example, in circumstances where it is required that appropriate concentrations of the desired compounds are delivered directly to the site in the body to be treated, administration may be regional rather than systemic. Regional administration provides the capability of delivering very high local concentrations of the desired compounds to the required site and thus is suitable for achieving the desired therapeutic or preventative effect whilst avoiding exposure of other organs of the body to the compounds and thereby potentially reducing side effects.

By way of example, administration according to embodiments of the invention may be achieved by any standard routes, including intracavitary, intravesical, intramuscular, intraarterial, intravenous, subcutaneous, topical or oral. Intracavitary administration may be intraperitoneal or intrapleural. In particular embodiments, administration may be via intravenous infusion or intraperitoneal administration.

In general, suitable compositions may be prepared according to methods which are known to those of ordinary skill in the art and may include pharmaceutically acceptable diluents, adjuvants and/or excipients. The diluents, adjuvants and excipients must be "acceptable" in terms of being compatible with the other ingredients of the composition, and not deleterious to the recipient thereof.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower is alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions.

For administration as an injectable solution or suspension, non-toxic parenterally acceptable diluents or carriers can include, Ringer's solution, medium chain triglyceride (MCT), isotonic saline, phosphate buffered saline, ethanol and 1,2 propylene glycol. For example, a commonly used carrier or vehicle for paclitaxel is Cremaphor EL. Paclitaxel is typically prepared in 50% Cremaphor EL and 50% ethanol.

Some examples of suitable carriers, diluents, excipients and adjuvants for oral use include peanut oil, liquid paraffin, sodium carboxymethylcellulose, methylcellulose, hydroxypropylmethylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose, hydroxypropylmethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethylcellulose, poly-vinylpyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The effective dose level of the administered compound for any particular subject will depend upon a variety of factors including: the type of tumour being treated and the stage of the tumour; the activity of the compound employed; the composition employed; the age, body weight, general health, sex and diet of the patient; the time of administration; the route of administration; the rate of sequestration of compounds; the duration of the treatment; drugs used in combination or coincidental with the treatment, together with other related factors well known in medicine.

One skilled in the art would be able, by routine experimentation, to determine an effective, non-toxic dosage which would be required to treat applicable conditions. These will most often be determined on a case-by-case basis.

For compositions of the present invention, the taxoid may be present in the composition in a concentration of at least about 1 pM. The concentration of the taxoid in the composition may be from about 1 pM to about 50 nM, from about 0.01 nM to about 10 nM, from about 0.05 nM to about 5 nM, or from about 0.1 nM to about 1 nM.

The benzimidazole carbamate compound may be present in the composition in a concentration of at least about 0.005 µM. The concentration of the benzimidazole carbamate in the composition may be from about 0.005 µM to about 10 µM, from about 0.01 µM to about 1 µM, from about 0.1 µM to about 0.5 µM, or from about 0.1 µM to about 0.25 µM.

Generally, an effective dosage of a composition for administration to a patient is expected to be in the range of about 0.01 mg to about 150 mg per kg body weight per 24 hours; typically, about 0.1 mg to about 150 mg per kg body weight per 24 hours; about 0.1 mg to about 100 mg per kg body weight per 24 hours; about 0.5 mg to about 100 mg per kg body weight per 24 hours; or about 1.0 mg to about 100 mg per kg body weight per 24 hours. More typically, an effective dose range is expected to be in the range of about 5 mg to about 50 mg per kg body weight per 24 hours.

Alternatively, an effective dosage may be up to about 5000 mg/m$^2$. Generally, an effective dosage is expected to be in the range of about 10 to about 5000 mg/m$^2$, typically about 10 to about 2500 mg/m$^2$, about 25 to about 2000 mg/m$^2$, about 50 to about 1500 mg/m$^2$, about 50 to about 1000 mg/m$^2$, or about 75 to about 600 mg/m$^2$.

Further, it will be apparent to one of ordinary skill in the art that the optimal quantity and spacing of individual dosages will be determined by the nature and extent of the condition being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

The present invention will now be further described in greater detail by reference to the following specific examples, which should not be construed as in any way limiting the scope of the invention.

EXAMPLES

Example 1

Paclitaxel and Albendazole Administration to Human Ovarian Carcinoma Cells

Human ovarian carcinoma cell lines OVCAR-3, SKOV-3, 1A9 and 1A9PTX22 were used. OVCAR-3 and SKOV-3 cells were obtained from the American Type Culture Collection (ATCC) and maintained on RPMI medium and McCoy5A medium respectively according to ATCC instructions. 1A9 is a clone of the human ovarian carcinoma cell line, A2780

(Sackett et al., 1997). 1A9PTX22 is a paclitaxel resistant subclone of 1A9 cells, isolated as an individual clone in a single step selection by exposing 1A9 cells to 5 ng/ml paclitaxel in the presence of 5 μg/ml verapamil, a Pgp antagonist (Giannakaou et al., 1997). Cells were maintained in 15 ng/ml paclitaxel and 5 μg/ml verapamil continuously.

Sulforhodamine B (SRB) colorimetric assay was used to study the effect of albendazole, paclitaxel or their combination on tumour cell cytotoxicity in vitro.

Cells were harvested from exponential phase cultures by trypsinization, counted and plated in 96-well plates. Optimal seeding densities for each cell line were determined to ensure exponential growth during a 5-day assay. Seeding densities were 5000, 1000, 400 and 3500 cells per well for OVCAR-3, SKOV-3, 1A9 and 1A9PTX22 cells, respectively. Cells plated in 96-well tissue culture plates were treated with 100 μl cell culture medium containing various concentrations of albendazole, paclitaxel or a combination of the two. Both albendazole and paclitaxel were originally made up in absolute ethanol and subsequently diluted with cell culture medium to give the desired drug concentrations with a final ethanol concentration of 1%. Treatment media were replaced on alternate days. At the end of the treatment period (5 days), wells were assayed for cellular protein content. The SRB assay was performed according to the method described by Skehan et al. (1990) and Papazisis at al. (1997), with minor modifications. The culture medium was aspirated prior to fixation of the cells by the addition of 100 μl 10% cold trichloroacetic acid. After an hour incubation at 4° C., cells were washed five times with water. The cells were then stained with 200 μl 0.4% SRB dissolved in 1% acetic acid for at least 15 min and subsequently washed four times with 1% acetic acid to remove unbound stain. The plates were left to dry at room temperature and bound protein stain was solubilized with 100 μl 10 mM un-buffered Tris base [tris(hydroxymethyl)aminomethane)] before reading the optical density (OD) at 570 nm.

For each of the four cell lines used in this study, sensitivity of each line was initially tested by incubating cells with various concentrations of albendazole or paclitaxel for 5 days. The SRB assay was performed at the end of the treatment period to determine cell response to drug treatment.

Data from OVCAR-3 cells are presented in FIG. 1, where response to various doses of albendazole is depicted in FIG. 1A and response to various doses of paclitaxel alone or in combination with albendazole (0.25 μM) is presented in FIG. 1B. As can be seen from FIG. 1B, the addition of 0.25 μM albendazole to the paclitaxel containing incubation medium led to a complete halt of cell proliferation.

Figure 2:
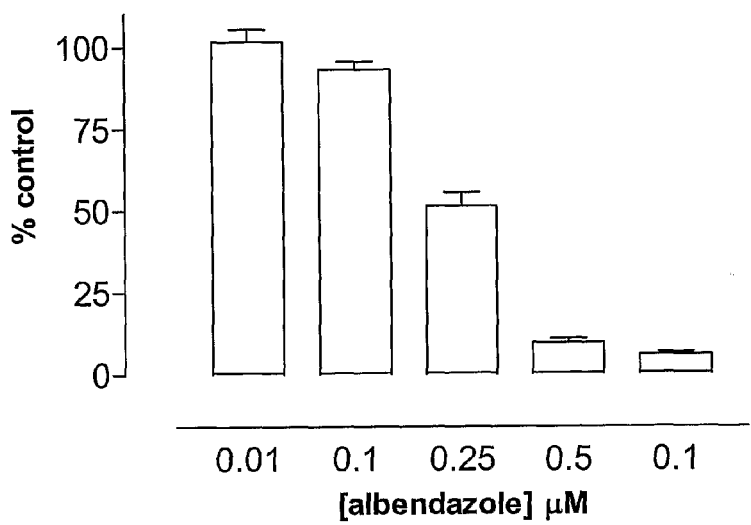
FIG. 2: Cytotoxic activity of albendazole and paclitaxel in inhibiting proliferation of SKOV-3 cells in vitro. (A) Dose-response inhibition of cell proliferation by albendazole alone. (B) Dose-related inhibition of proliferation by paclitaxel and potentiation of this effect when cells were co-incubated with 0.25 µM albendazole. Cell proliferation was measured using a sulforhodamine B assay. Results are presented as the % of control (vehicle treated cells).
Figure 2:
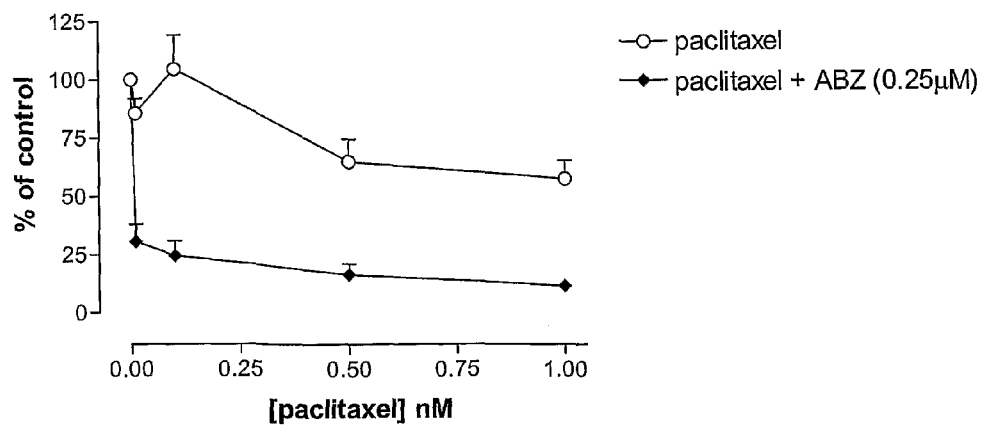

SKOV-3 cells (FIGS. 2A and 2B) responded to albendazole, paclitaxel or the combination in a similar fashion. A dose-response inhibition of cell proliferation by paclitaxel was profoundly potentiated upon co-incubation with albendazole. Treatment of these cells with 0.01 nM paclitaxel alone led to 14.5% inhibition of cell proliferation and with 0.25 μM albendazole alone to a 48.4% reduction. Upon co-incubation with paclitaxel (0.01 nM) and albendazole (0.25 μM) there was 69.4% reduction in cell proliferation (p<0.001 compared to paclitaxel alone).

Figure 3:
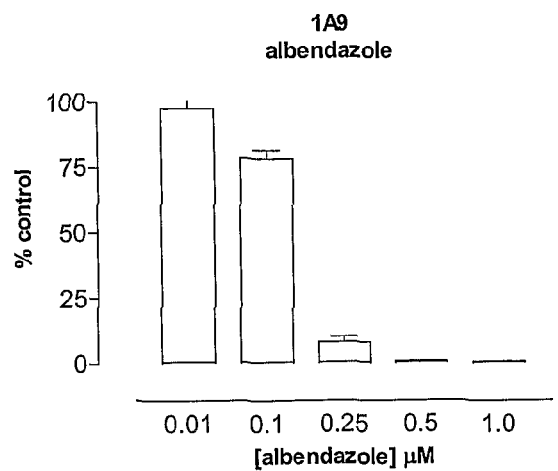
FIG. 3: Cytotoxic activity of albendazole and paclitaxel in inhibiting proliferation of 1A9 cells in vitro. (A) Dose-response inhibition of cell proliferation by albendazole alone. (B) Dose-related inhibition of proliferation by paclitaxel alone. (C) Combined effect of co-incubation of 1A9 cells with varying doses of paclitaxel and 0.1 µM albendazole. Cell proliferation was measured using a sulforhodamine B assay. Results are presented as the % of control (vehicle treated cells).
Figure 3:
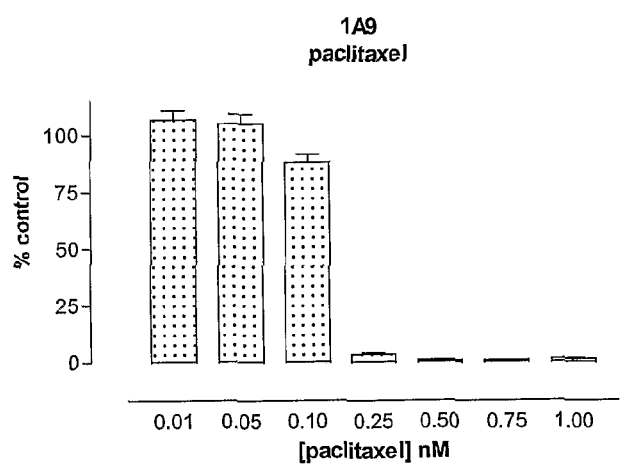
Figure 3:
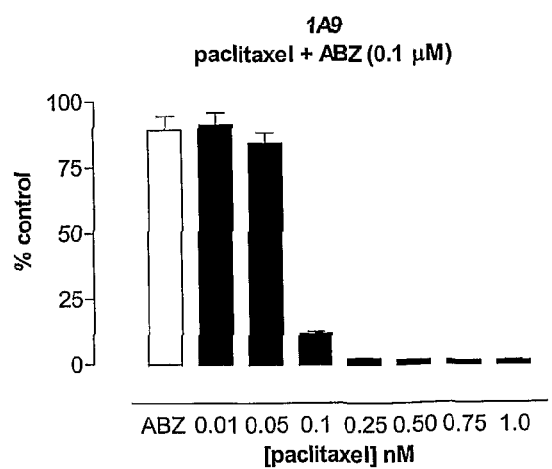

This inhibitory effect was more intense in 1A9 cells (FIG. 3), where treatment with a low albendazole concentration of 0.1 μM alone (FIG. 3A) or treatment with 0.1 nM paclitaxel alone (FIG. 3B) led to 11.8% and 21.8% inhibition respectively. Co-incubation of the cells with the two drugs at these concentrations led to 87.7% inhibition of proliferation (p<0.001) (FIG. 3C).

Figure 4:
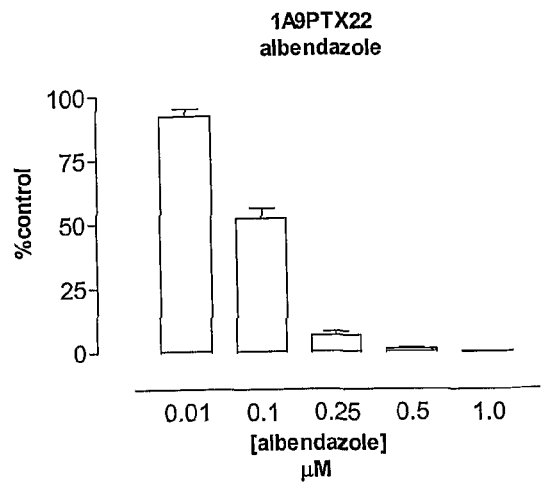
FIG. 4: Cytotoxic activity of albendazole and paclitaxel in inhibiting proliferation of 1A9PTX22 cells in vitro. (A) Dose-response inhibition of cell proliferation by albendazole alone. (B) Dose-related inhibition of proliferation by paclitaxel alone, (C) Combined effect of co-incubation of 1A9 cells with varying doses of paclitaxel and 0.1 µM albendazole. Cell proliferation was measured using a sulforhodamine B assay. Results are presented as the % of control (vehicle treated cells).
Figure 4:
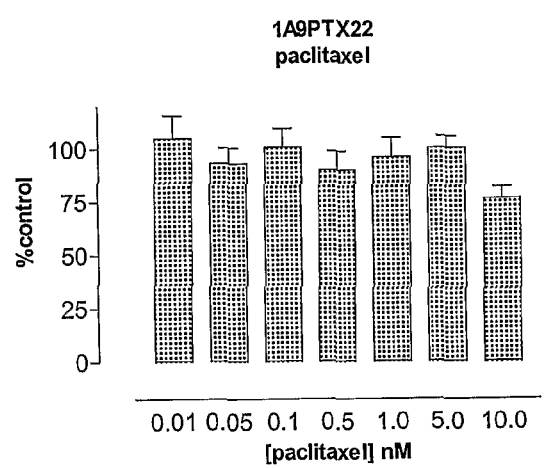
Figure 4:
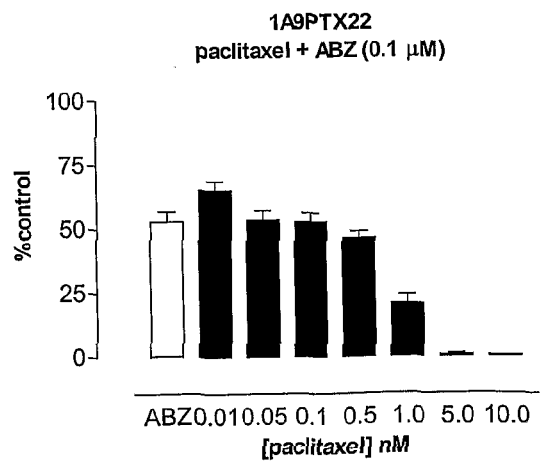

Treatment of 1A9PTX22, a paclitaxel resistant sub-line of 1A9, with various concentrations of albendazole revealed the extra sensitivity of these cells to albendazole on one hand (FIG. 4A) and confirmed the resistant nature of the cells to paclitaxel on the other (FIG. 4B). From these results it can be seen that, compared to the parent line (1A9), the paclitaxel resistant sub-line 1A9PTX22 is even more sensitive to albendazole. The addition of a low concentration (0.1 μM) of albendazole to medium containing various concentrations of paclitaxel had a dramatic effect on cell proliferation (FIG. 4C). Whereas cell proliferation was not affected by the addition of 1.0 nM or 5.0 nM paclitaxel alone, at the same paclitaxel concentrations, co-incubation with albendazole (0.1 μM) led to 79.1% inhibition of cell proliferation at 1.0 nM paclitaxel and 99.1% inhibition of cell proliferation at 5.0 nM paclitaxel. Treatment with albendazole alone at 01 μM had a 53% inhibitory effect on proliferation of these cells.

Example 2

Cross Resistance in Paclitaxel Resistant Cell Line

Taxoids, such as paclitaxel, are one class of antimitotic drugs that target tubulin. A further well-characterized class of tubulin-binding drugs are the Vinca alkaloids, exemplified by vincristine, vinblastine and vinorelbine. The Vinca alkaloids interfere with a cells ability to properly form the mitotic spindle by preventing the normal polymerization of microtubules. They have importance in the treatment of leukemia, lymphomas, small cell lung cancer, and other malignancies. A third class of anti-tubulin drugs, exemplified by colchicine, is comprised of a structurally diverse collection of small molecules that are related by the fact that all bind to a common site on tubulin known as the colchicine site and prevent the normal polymerization of microtubules.

As described above in Example 1, the present inventors have shown that the paclitaxel resistant cell line 1A9PTX22 displays increased sensitivity to the antiproliferative effects of albendazole compared to the paclitaxel sensitive parent line 1A9. To investigate the properties of 1A9PTX22 cells further the inventors investigated the level of sensitivity of these cells to representatives of two other classes of antimitotic drugs, namely vincristine and colchicine.

Figure 5:
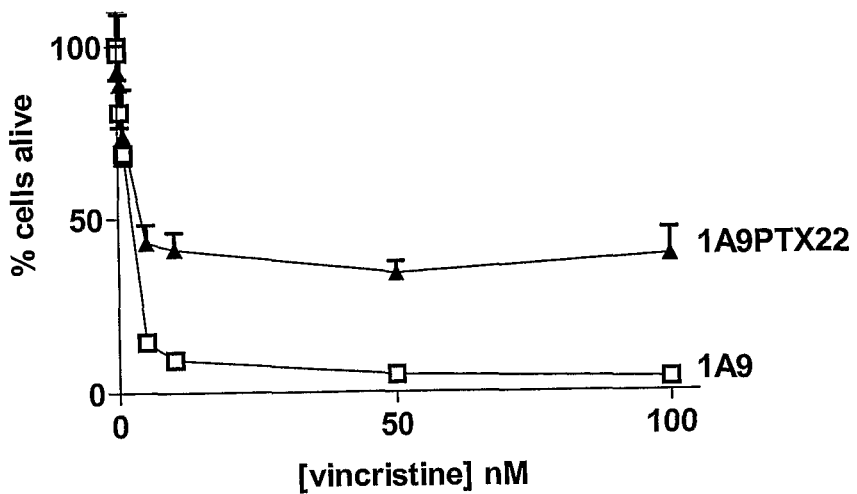
FIG. 5: Cytotoxic activity of vincristine (A) and colchicine (B) in inhibiting proliferation of 1A9 and 1A9PTX22 cells in vitro. Concentrations of vincristine (A) shown are 0.1 nM, 0.5 nM, 1 nM, 5 nM, 10 nM, 50 nM and 100 nM. Concentrations of colchicine (B) shown are 0.1 nM, 0.5 nM, 1 nM, 5 nM, 10 nM, 50 nM, 100 nM, 500 nM and 1000 nM. Cell proliferation was measured using a sulforhodamine B assay—the percentage of cells alive (cell growth) was calculated by defining the optical density of untreated cells (control) as 100%. Values represent the mean±SD of 8 replicate experiments, each repeated at least twice.
Figure 5:
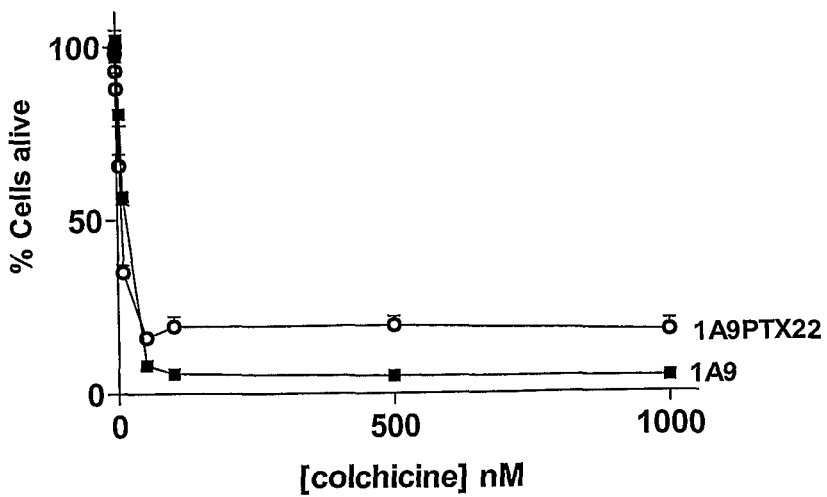

1A9 and 1A9PTX22 cells plated in 96-well tissue culture plates were treated with 100 μl cell culture medium containing various concentrations of vincristine and colchicine for 72 hours and SRB assays conducted as described above. As for paclitaxel (see Example 1), both vincristine and colchicine were originally made up in absolute ethanol and subsequently diluted with cell culture medium to give the desired drug concentrations with a final ethanol concentration of 1%. The results are illustrated in FIGS. 5A (vincristine) and 5B (colchicine). The degree of sensitivity of 1A9PTX22 cells to both vincristine and colchicine is significantly reduced when compared to that of the parent cell line 1A9. The partial resistance of 1A9PTX22 is apparent for vincristine at concentrations of 5 nM and above and for colchicine at 100 nM and above (p<0.001).

Example 3

Compositions for Treatment

In accordance with the best mode of performing the invention provided herein, specific preferred compositions are outlined below. The following are to be construed as merely illustrative examples of compositions and not as a limitation of the scope of the present invention in any way.

Example 3(A)

Composition for Parenteral Administration

A composition for parenteral injection could be prepared to contain 0.05 mg to 5 g of albendazole and 0.05 mg to 5 g of paclitaxel in 10 mls to 2 liters of 0.1-10% carboxymethylcellulose.

Similarly, a composition for intravenous infusion may comprise 250 ml of sterile Ringer's solution, and 0.05 mg to 5 g of albendazole and 0.05 mg to 5 g of paclitaxel.

Example 3(B)

Composition for Oral Administration

A composition of a suitable agent in the form of a capsule may be prepared by filling a standard two-piece hard gelatin capsule with 500 mg of albendazole, in powdered form, 500 mg of paclitaxel, 100 mg of lactose, 35 mg of talc and 10 mg of magnesium stearate.

REFERENCES

Giannakakou, P., Sackett, D. L., Kang, Y. K., Zhan, Z., Buters, J. T., Fojo, T., and Poruchynsky, M. S. Paclitaxel-resistant human ovarian cancer cells have mutant beta-tubulins that exhibit impaired paclitaxel-driven polymerization. *Journal of Biological Chemistry*, 272: 17118-17125, 1997.

Horton, J. Albendazole: a review of anthelmintic efficacy and safety in humans. *Parasitology*, 121, 2000.

Lacey, E. Mode of action of benzimidazoles. Parasitol. Today, 6: 112-115, 1990.

Lacey, E. and Gill, J. H. Biochemistry of benzimidazole resistance. *Acta Tropica*, 56: 245-262, 1994.

Markman, M. Management of toxicities associated with the administration of taxanes. *Expert Opinion on Drug Safety*, 2: 141-146, 2003.

Mekhail, T. M. and Markman, M. Paclitaxel in cancer therapy. *Expert Opinion on Pharmacotherapy*, 3: 755-766, 2002.

Papazisis, K. T., Geromichalos, G. D., Dimitriadis, K. A., and Kortsaris, A. H. Optimization of the sulforhodamine B colorimetric assay. *Journal of Immunological Methods*, 208: 151-158, 1997.

Sackett, D. L., Giannakakou, P., Poruchynsky, M., and Fojo, A. Tubulin from paclitaxel-resistant cells as a probe for novel antimicrotubule agents. *Cancer Chemotherapy & Pharmacology*, 40: 228-232, 1997.

Skehan, P., Storeng, R., Scudiero, D., Monks, A., McMahon, J., Vistica, D., Warren, J. T., Bokesch, H., Kenney, S., and Boyd, M. R. New colorimetric cytotoxicity assay for anti-cancer-drug screening. *Journal of the National Cancer Institute*, 82: 1107-1112, 1990.

Yamazaki, S., Sekine, I., and Saijo, N. [Paclitaxel (taxol): a review of its antitumour activity and toxicity in clinical studies]. Gan to Kagaku Ryoho [*Japanese Journal of Cancer & Chemotherapy*], 25: 605-615, 1998.

What is claimed is:

1. A method for the treatment of an ovarian tumor in a subject, the method comprising administering to the subject an effective amount of paclitaxel and an effective amount of albendazole wherein the administration of paclitaxel and albendazole has an additive and/or synergistic anti-tumor effect.

2. A method for the treatment of a taxoid-insensitive ovarian tumor in a subject, the method comprising systemically administering to the subject paclitaxel and an effective amount of albendazole wherein the administration of paclitaxel and albendazole has an additive and/or synergistic anti-tumor effect.

3. The method of claim 2 wherein the paclitaxel is administered in an amount ineffective to treat the ovarian tumor if administered alone.

4. A method for the treatment of an ovarian tumor in a subject, the method comprising administering to a subject having an ovarian tumor an effective amount of at least one taxoid and an effective amount of at least one benzimidazole carbamate compound, wherein the benzimidazole carbamate compound is albendazole, and the taxoid is paclitaxel.

5. The method of claim 4 wherein the ovarian tumor is insensitive to treatment with one or more antimitotic drugs.

6. The method of claim 5 wherein the one or more antimitotic drugs are selected from the group consisting of a taxoid, a Vinca alkaloid and a colchicinoid.

7. The method of claim 5 wherein the ovarian tumor is a taxoid-insensitive ovarian tumor.

8. The method of claim 4 wherein the taxoid and the benzimidazole carbamate compound are administered simultaneously.

9. The method of claim 4 wherein the taxoid and the benzimidazole carbamate compound are administered sequentially.

10. The method of claim 4 wherein the taxoid and the benzimidazole carbamate are administered systemically.

* * * * *